(12) United States Patent
Gilliam-Perkins

(10) Patent No.: US 10,980,906 B2
(45) Date of Patent: Apr. 20, 2021

(54) DEVICE FOR REDUCING GERMS ON A WRITING INSTRUMENT OR STYLUS

(71) Applicant: Miriah Gilliam-Perkins, Southfield, MI (US)

(72) Inventor: Miriah Gilliam-Perkins, Southfield, MI (US)

( * ) Notice: Subject to any disclaimer, the term of this patent is extended or adjusted under 35 U.S.C. 154(b) by 0 days.

(21) Appl. No.: 16/468,770

(22) PCT Filed: Dec. 21, 2017

(86) PCT No.: PCT/US2017/067869
§ 371 (c)(1),
(2) Date: Jun. 12, 2019

(87) PCT Pub. No.: WO2018/125744
PCT Pub. Date: Jul. 5, 2018

(65) Prior Publication Data
US 2019/0314536 A1  Oct. 17, 2019

Related U.S. Application Data

(60) Provisional application No. 62/498,641, filed on Dec. 30, 2016.

(51) Int. Cl.
*A61L 2/24* (2006.01)
*A61L 2/10* (2006.01)
*A61L 2/28* (2006.01)

(52) U.S. Cl.
CPC *A61L 2/24* (2013.01); *A61L 2/10* (2013.01); *A61L 2/28* (2013.01)

(58) Field of Classification Search
USPC .................................................. 250/455.11
See application file for complete search history.

(56) References Cited

U.S. PATENT DOCUMENTS

| | | | |
|---|---|---|---|
| 5,928,665 A * | 7/1999 | Cercone | A01N 59/12 424/404 |
| 6,039,928 A * | 3/2000 | Roberts | A61L 2/10 422/186.3 |
| 6,190,078 B1 * | 2/2001 | Smith | B43K 23/001 401/131 |
| 8,058,629 B2 * | 11/2011 | Long | A61L 2/10 250/455.11 |
| 8,357,914 B1 * | 1/2013 | Caldwell | A61L 2/10 250/455.11 |
| 9,000,398 B2 * | 4/2015 | Nelson | A61L 2/10 250/455.11 |
| 10,857,254 B2 * | 12/2020 | Graupner | F21V 7/005 |

(Continued)

*Primary Examiner* — Phillip A Johnston
(74) *Attorney, Agent, or Firm* — Kohn & Associates PLLC

(57) ABSTRACT

A germ-reducing pen container including a body having a hollow passageway extending therethrough from an insertion end to a distal end for receiving a pen, the hollow passageway having at least one ultraviolet C light operatively attached thereto, an indicator on an outer surface of the body, and a dispensing mechanism operatively attached at the insertion end for dispensing the pen. A method of reducing germs on a pen, by inserting a pen into a body of a germ-reducing pen container, applying ultraviolet C light to the pen, killing the germs on the pen, indicating that the pen has been cleaned, and dispensing the pen.

16 Claims, 2 Drawing Sheets

(56) References Cited

U.S. PATENT DOCUMENTS

2010/0322699 A1* 12/2010 Dam .................. A61L 2/18
  401/196
2014/0245866 A1* 9/2014 Hadlock ............... A61L 2/10
  81/9.2

* cited by examiner

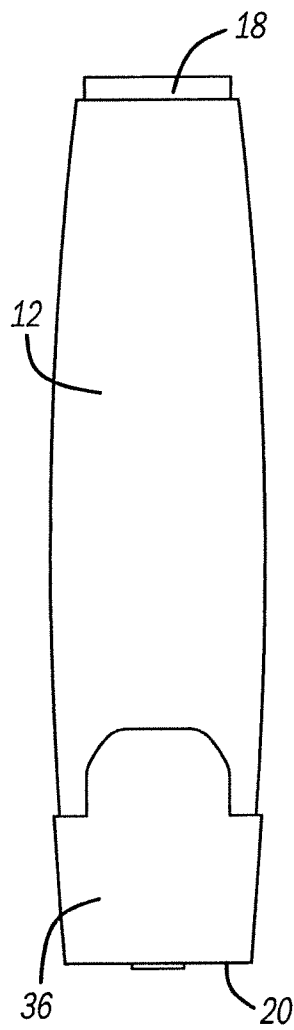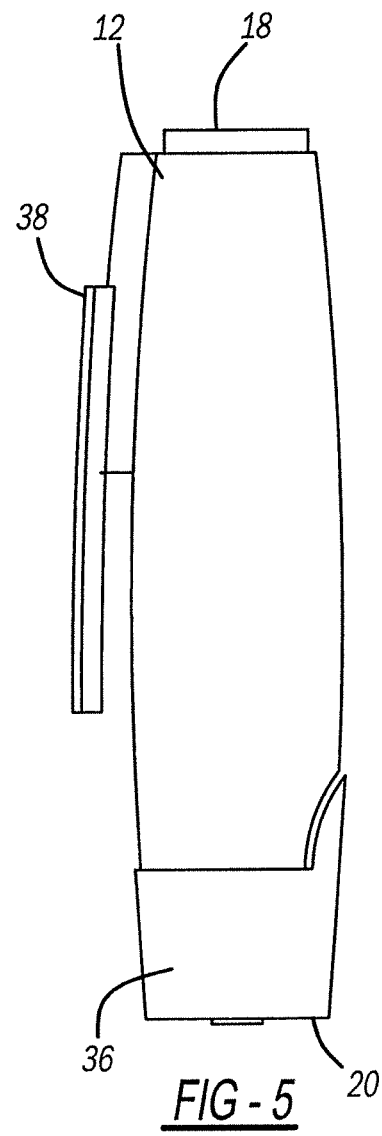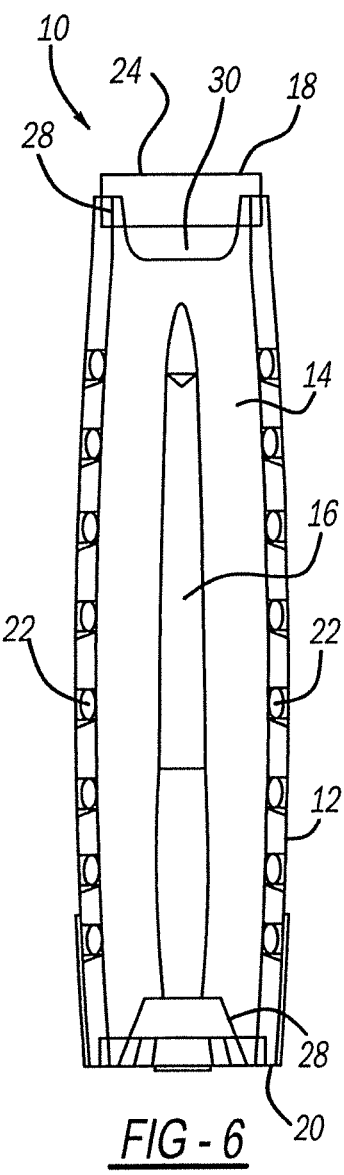

DEVICE FOR REDUCING GERMS ON A WRITING INSTRUMENT OR STYLUS

BACKGROUND OF THE INVENTION

1. Technical Field

The present invention relates to containers for pens. More specifically, the present invention relates to containers and methods for reducing germs on pens.

2. Background Art

Many every day objects pick up germs from people touching them, especially when those objects are in a public place where multiple people use them. For example, grocery carts are handled by many people during the day. Many stores have started providing sanitizing wipes for people to clean handlebars when they take a cart. Similarly, pens can be used by multiple people during the day in banks, medical offices, or any place where people sign in for an appointment or sign documents. However, there is currently not a device that can sanitize pens easily between uses.

There remains a need for a device that can remove germs from pens or writing instruments to reduce and/or prevent the spread of germs.

SUMMARY OF THE INVENTION

The present invention provides for a germ-reducing pen container including a body having a hollow passageway extending therethrough from an insertion end to a distal end for receiving a pen, the hollow passageway having at least one ultraviolet C light operatively attached thereto, an indicator on an outer surface of the body, and a dispensing mechanism operatively attached at the insertion end for dispensing the pen.

The present invention also provides for a method of reducing germs on a pen, by inserting a pen into a body of a germ-reducing pen container, applying ultraviolet C light to the pen, killing the germs on the pen, indicating that the pen has been cleaned, and dispensing the pen.

DESCRIPTION OF THE DRAWINGS

Other advantages of the present invention are readily appreciated as the same becomes better understood by reference to the following detailed description when considered in connection with the accompanying drawings wherein:

FIG. 4 is a side view of the body of the germ-reducing pen container;

FIG. 5 is a side view of the body of the germ-reducing pen container with a clip; and FIG. 6 is a cross-sectional view of the germ-reducing pen container holding a pen with an alternative embodiment of ultraviolet C lights.

DETAILED DESCRIPTION OF THE INVENTION

The present invention generally provides for a germ-reducing pen container (shown at 10 in the FIGURES) that reduces and/or removes germs from pens or other writing instruments and protects users from the spread of bacteria and viruses.

Figure 1:
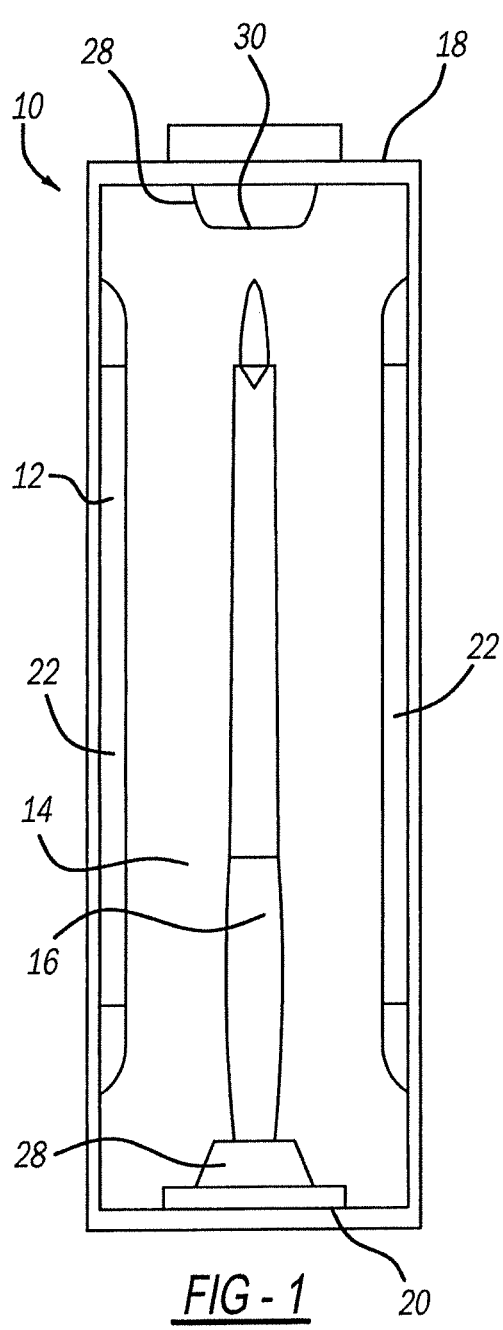
FIG. 1 is cross-sectional view of the germ-reducing pen container holding a pen.

As shown in FIG. 1, the germ-reducing pen container 10 includes a body 12 and a hollow passageway 14 extending therethrough from an insertion end 18 to a distal end 20 for receiving a pen 16. The hollow passageway 14 includes at least one ultraviolet C (UVC) light 22 operatively attached thereto. The body 12 further includes an indicator 24 on an outer surface 26, and a dispensing mechanism 28 at the insertion end 18.

The body 12 is preferably made of plastic that can withstand UVC light, metal, or any other suitable material. The body 12 can hold a single pen 16 or multiple pens 16 in the hollow passageway 14, and can be any appropriate size. The body 12 can include any necessary electronics, circuitry, and power sources used to operate the germ-reducing pen container 10. For example, the body 12 can include a USB rechargeable battery and USB port 32 (shown in FIG. 3) or other rechargeable batteries and battery pack 36 (shown in FIGS. 4 and 5) located at any suitable place on the body 12, such as the distal end 20. The body 12 can be substantially rectangular (FIGS. 1-3) or oblong (FIGS. 4-6) shaped. The germ-reducing pen container 10 can sit on a desktop and/or can be portable.

The hollow passageway 14 is of a size and shape that can receive at least one pen 16. In other words, the hollow passageway 14 is substantially pen-shaped or stylus-shaped as a long cylindrical passageway. The hollow passageway 14 can include any suitable sensors that can detect the presence of a pen 16. The hollow passageway 14 is open at the insertion end 18 to receive the pen 16, and closed at the distal end 20.

The pen 16 can be a stylus pen, but can also be a fountain pen or any other suitable pen. While a pen 16 is used throughout the description, it should be understood that other writing instruments can also be used, such as pencils, mechanical pencils, a stylus, or markers. The pen 16 can optionally include a cord that keeps the pen 16 attached to a desktop for public use.

An antimicrobial sponge 30 can be included operatively attached to the insertion end 18 at the hollow passageway 14 to clean off any visible germs during the initial insertion of the pen 16 into the germ-reducing pen container 10. The antimicrobial sponge can change color indicating that it is time or due to be changed and replaced with a new antimicrobial sponge. The antimicrobial sponge can also optionally be omitted from the body 12.

The ultraviolet C lights 22 are germicidal lights. Once the pen 16 is inside the germ-reducing pen container 10, the ultraviolet C lights 22 turn on for a duration of time required to complete the cleaning process and kill bacteria and viruses or any other germs present on the pen 16. The ultraviolet C lights 22 can be operatively attached within the hollow passageway 14, such as in a radial design (FIG. 1), rows of multiple ultraviolet C lights along the hollow passageway 14 (FIG. 6), or any other suitable design. The ultraviolet C lights 22 can be the length of the hollow passageway 14 or any other suitable size.

Figure 2:
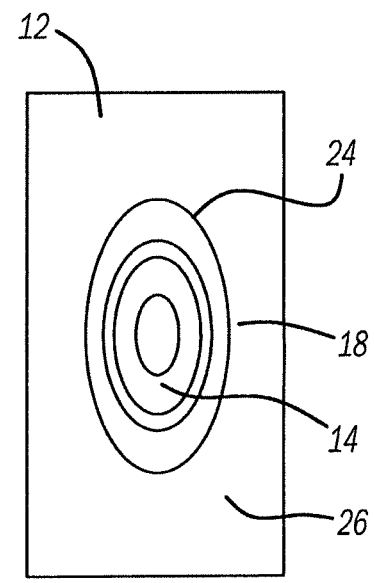
FIG. 2 is a front view of an insertion end of the germ-reducing pen container.
Figure 3:
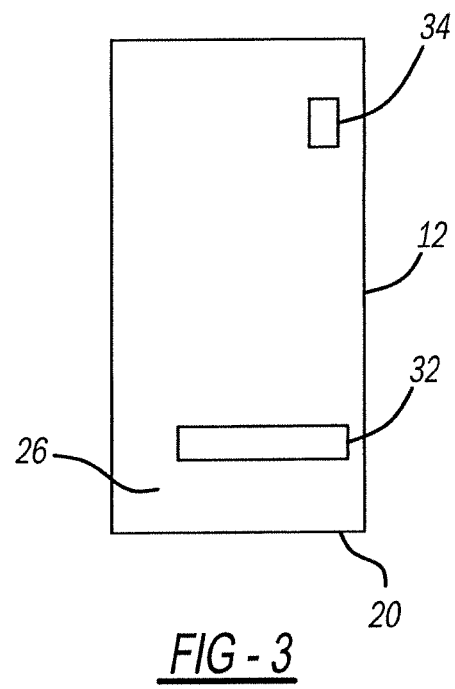
FIG. 3 is a front view of a distal end of the germ-reducing pen container.

The indicator 24 shows the status of the pen 16 on an outside surface 26 of the body 12 and is preferably a light 24 as shown in FIG. 2, surrounding the hollow passageway 14 at the insertion end 18. The indicator 24 can be located at any other suitable place. For example, the indicator can be a red light while the pen 16 is being cleaned. The indicator can turn green when the pen 16 is ready for use. Other indicators can also be used, such as sound.

The dispensing mechanism 28 dispenses the cleaned pen 16 out of the insertion end 18, displaying that the pen 16 is ready for use. The dispensing mechanism 28 can use a flywheel, and/or a spring to dispense the pen 16. Elements of the dispensing mechanism 28 can also be situated at the distal end 20 in order to help dispense the pen 16 through the insertion end 18.

An on/off switch 34 (shown in FIG. 3) can be located on any suitable place (such as the distal end 20) on the pen container 10 in order to operate and power the pen container 10. The on/off switch 34 is in electronic connection with any battery pack 36 or USB port and battery 32.

A clip 38 can be operatively attached to the body 12 near the insertion end 18 to allow the germ-reducing pen container 10 to be secured in a pocket, backpack, bag, or folder. The clip 38 can be metal or plastic and the same material as the body 12 or a different material.

The germ-reducing pen container 10 can be used in many different places, such as, but not limited to, hospitals, doctor's offices, schools, businesses, markets, or banks.

The present invention also provides for a method of reducing germs on a pen, by inserting a pen 16 into a body 12 of a germ-reducing pen container 10, applying ultraviolet C light to the pen 16, killing (or at least reducing) the germs on the pen 16, indicating that the pen 16 has been cleaned, and dispensing the pen 16. The method can optionally include the step of swiping the pen 16 with an antimicrobial sponge 30 during the insertion step to reduce germs on the pen as well. Upon inserting the pen 16 into the body 12, sensors in the hollow passageway 14 can detect the presence of the pen 16 and can actuate the cleaning process by turning on the ultraviolet C lights for a period of time that allows germs to be killed or reduced. The indicator 24 as a light can turn on to indicate that the pen 16 has been cleaned. The pen 16 can then be dispensed outside of the body 12 by the dispensing mechanism 28.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A germ reducing pen container comprising:
    a body including a hollow passageway extending therethrough from an insertion end to a closed distal end for receiving a pen, the hollow passageway having at least one ultraviolet C light operatively attached thereto;
    an indicator on an outer surface of said body of a light surrounding said hollow passageway at said insertion end; and
    a dispensing mechanism operatively attached at said insertion end for dispensing said pen out of said insertion end, wherein when said pen is inserted into said container, said pen is exposed to ultraviolet C light for a period of time that reduces germs on said pen, and wherein said container is portable and includes a USB port and USB rechargeable battery.

2. The germ reducing pen container of claim 1, wherein said body is a shape chosen from rectangular and oblong.

3. The germ reducing pen container of claim 1, wherein said body can hold multiple pens within said hollow passageway.

4. The germ reducing pen container of claim 1, wherein said germ reducing pen container is portable.

5. The germ reducing pen container of claim 1, wherein said hollow passageway is open at said insertion end and closed at said distal end.

6. The germ reducing pen container of claim 1, wherein said hollow passageway is substantially pen-shaped.

7. The germ reducing pen container of claim 1, further including an antimicrobial sponge operatively attached to said insertion end at said hollow passageway.

8. The germ reducing pen container of claim 7, wherein said antimicrobial sponge changes color when due to be replaced.

9. The germ reducing pen container of claim 1, wherein said at least one ultraviolet C light is attached in a radial design around said hollow passageway.

10. The germ reducing pen container of claim 1, wherein multiple ultraviolet C lights are operatively attached in rows along said hollow passageway.

11. The germ reducing pen container of claim 1, wherein said dispensing mechanism includes a mechanism chosen from the group consisting of flywheel, spring, and combinations thereof.

12. The germ reducing pen container of claim 1, further including an on/off switch operatively attached to said body.

13. The germ reducing pen container of claim 1, further including a clip operatively attached to said body.

14. A method of reducing germs on a pen, including the steps of:
    inserting a pen into a body of a portable USB rechargeable germ reducing pen container through an insertion end into a hollow passageway extending through the body from the insertion end to a closed distal end;
    applying ultraviolet C light to the pen for a period of time that reduces the germs on the pen;
    killing the germs on the pen;
    indicating that the pen has been cleaned with a light surrounding the hollow passageway at the insertion end; and
    dispensing the pen out through the insertion end.

15. The method of claim 14, wherein said inserting step further includes the step of swiping the pen with an antimicrobial sponge and reducing germs on the pen.

16. The method of claim 14, after said inserting step, further including the step of detecting the presence of a pen within a hollow passageway of the body, and actuating ultraviolet C lights.

* * * * *